United States Patent [19]

Morita et al.

[11] 4,031,388

[45] June 21, 1977

[54] METHOD FOR THE ANALYSIS OF ISOTOPES

[75] Inventors: Masato Morita; Reiko Morita, both of Suita; Kiyoteru Otozai, Toyonaka, all of Japan

[73] Assignee: International Nuclear Fuel Co., Ltd., Toyonaka, Japan

[22] Filed: Sept. 6, 1974

[21] Appl. No.: 503,693

[30] Foreign Application Priority Data

Sept. 8, 1973 Japan .................. 48-101488

[52] U.S. Cl. .................. 250/272; 250/306
[51] Int. Cl.$^2$ .................. G01N 23/20
[58] Field of Search .................. 250/272, 273, 306

[56] References Cited

UNITED STATES PATENTS

| | | | |
|---|---|---|---|
| 2,908,821 | 10/1959 | Schumacher | 250/273 |
| 2,928,944 | 3/1960 | Reiffel | 250/273 |
| 3,171,961 | 3/1965 | Yule | 250/269 |
| 3,257,558 | 6/1966 | Cook et al. | 250/272 |
| 3,710,104 | 1/1973 | Pavlik | 250/272 |

OTHER PUBLICATIONS

Source Book on Atomic Energy Chap. IV, pp. 110–113 by Glasstone 2nd Edition 1958.
Activation Analysis by High Energy Particles by Tilbury et al., Nucleonics, Sept. 1965, pp. 70–72.
Source Book on Atomic Energy by Glasstone, pp. 286, 287.

*Primary Examiner*—Harold A. Dixon
*Attorney, Agent, or Firm*—Birch, Stewart, Kolasch and Birch

[57] ABSTRACT

A method for the qualitative or quantitative analysis of isotopes, characterized by bombarding a substance with X rays or electrons of a previously determined dose and energy for analyzing an isotope in the substance to be detected or measured, to produce an excited state of atomic nuclei of the isotope and thereafter detecting the existence or measuring the dose of the gamma rays or internal conversion electrons emitted in the course of the deexcitation process of the atomic nuclei in the excited state to the ground state. According to the present invention, a particular isotope or element in a substance can qualitatively or quantitatively by analyzed in a simple and precise manner within an extremely short period of time without the necessity of using a large scale apparatus.

4 Claims, 1 Drawing Figure

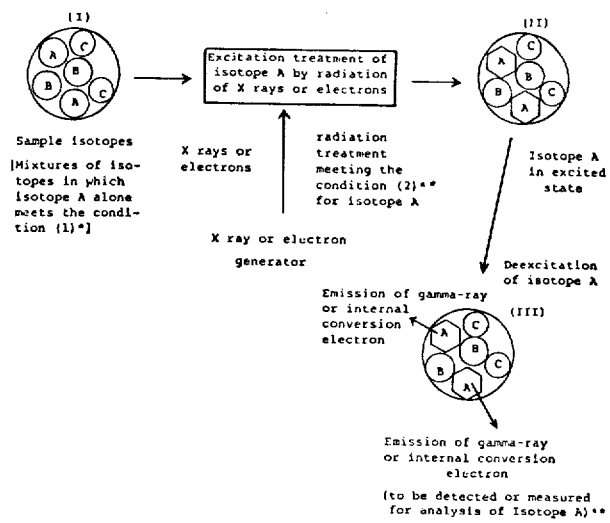

\* The condition (1) set forth in the claims for isotopes the atomic nuclei of which are to be excited \*\* The condition (2) set forth in the claims for radiation of X rays or electrons to cause excitation of the atomic nuclei or the isotope A \*\*\* If the presence or dose of the secondary radioactivity emitted as internal conversion electron or gamma-ray is detected or measured, qualitative' or quantitative analysis of Isotope A can be attained at a high accuracy.

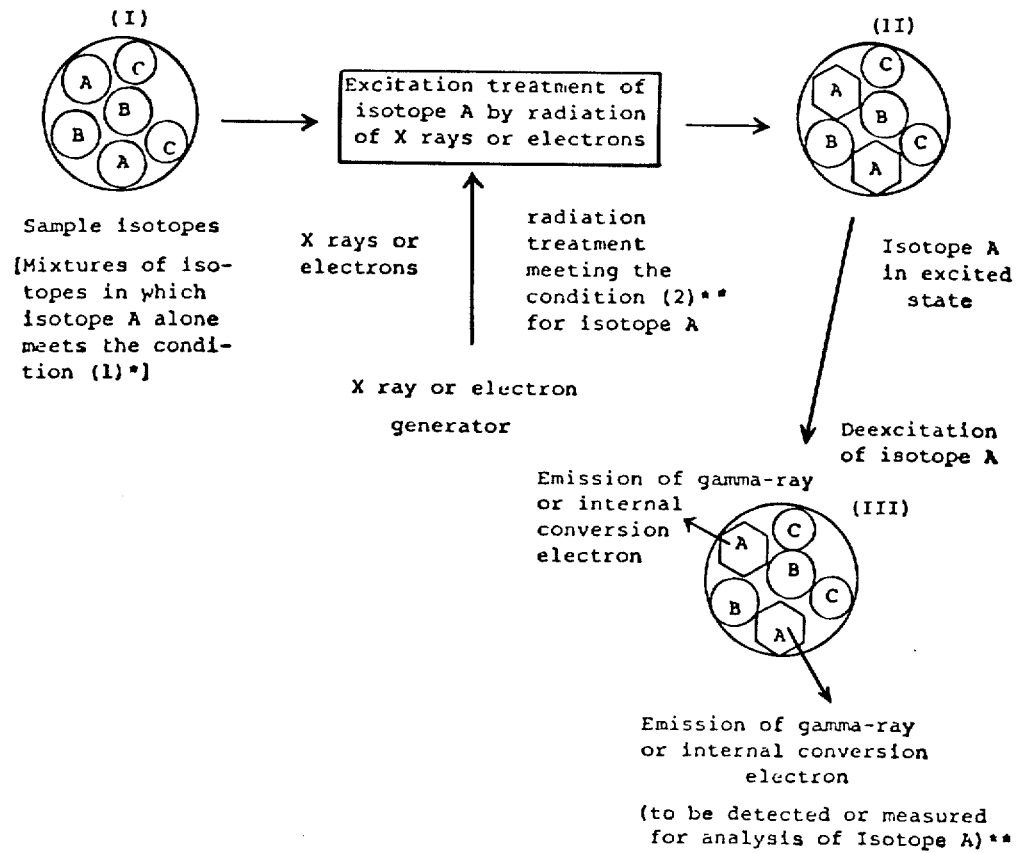

* The condition (1) set forth in the claims for isotopes the atomic nuclei of which are to be excited

** The condition (2) set forth in the claims for radiation of X rays or electrons to cause excitation of the atomic nuclei or the isotope A

*** If the presence or dose of the secondary radioactivity emitted as internal conversion electron or gamma-ray is detected or measured, qualitative or quantitative analysis of Isotope A can be attained at a high accuracy.

METHOD FOR THE ANALYSIS OF ISOTOPES

BACKGROUND OF THE INVENTION

The present invention relates to a method for the quantitative or qualitative analysis of isotopes. More particularly, the present invention relates to a method for the qualitative or quantitative analysis of particular isotopes by detecting the existence the gamma ray or internal conversion electrons emitted from the isotope in the excited state or by quantitively analyzing the emission dose of the gamma rays or internal conversion electrons.

The prior art methods developed hitherto for the quantitative analysis of isotopes include those utilizing a certain kind of physical means taking advantage of the difference in mass among isotopes, for example, mass spectrometry utilizing the Lorentz force for charged particles under the influence of the electromagnetic fields. In general, however, these prior art methods utilizing the difference in mass among isotopes require relatively large apparatus or equipment for making measurement and furthermore, it is difficult to obtain the quantitative analysis of isotopes in a precise manner within a short period of time.

BRIEF SUMMARY OF THE INVENTION

It is an object of the present invention to provide a method for the quantitative analysis of isotopes wherein disadvantages encountered in the prior art methods are overcome.

It is another object of the present invention to provide a method for the quantitative analysis of isotopes wherein the measurement is attained in a precise analysis of isotopes wherein the measurement is attained in a precise manner within a very short period of time using relatively small-scale apparatus.

It is still another object of the present invention to provide a method for the qualitative analysis of isotopes wherein the measurement is attained in a more simple manner within a very short period of time.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

It has now been found that the above mentioned objects can be attained by raising the atomic nuclei of a particular isotope from their ground state to their excited state and measuring the gamma ray or internal conversion electrons emitted when the atomic nuclei in the excited state are deexcited to the ground state.

In accordance with the present invention, there is provided a method for the qualitative or quantitative analysis of isotopes, characterized by bombarding a substance with X rays or electrons of a previously determined dose and energy for an isotope to be measured, to produce an excited state of atomic nuclei of the isotope in the substance and thereafter measuring the gamma ray or internal conversion electron emitted when the atomic nuclei in the excited state are deexcited to the ground state.

It has now been surprisingly found that the excited state of atomic nuclei can be produced in a comparatively simple manner by bombarding atoms with X rays or electrons under specific conditions without the necessity of using large scale apparatus, for example, atomic piles as used in the conventional methods. The atomic nuclei in the excited state emit gamma rays or internal conversion electrons in the course of deexcitation of said atomic nuclei from the excited state to the ground state. According to the method of the present invention, the existence of a particular isotope in a substance to be tested can easily be checked and the concentration of said isotope can also be determined by utilizing the above method of producing the excited state of atomic nuclei. In comparison with the mass spectrometry in the prior art techniques, the method of the present invention utilizing no physical means which takes advantage of the difference in mass among isotopes is indeed an epoch-making method for quantitatively analysis of isotopes as it enables the quantitative analysis in a precise manner within a very short period of time by the use of an extremely small scale apparatus. The qualitative or quantitative analysis according to the present invention is attained simply by counting the gamma-rays or internal conversion electrons emitted when the atomic nuclei in the excited state is deexcited to the ground state.

To produce the excited state of atomic nuclei according to the method of the present invention, (1) in the atoms selected to be produced in the excited state of their nuclei, (a) the difference between the nuclear excitation energy and the difference between the binding energies of adequately selected two electron orbits is small enough to introduce the nuclear excitation by electron transition, and (b) the system of the nucleus and the electrons in the case of ionizing the orbital electron in said atoms should satisfy the spin and parity conservation laws, and (2) the energy of the bombarding X ray or electrons should be larger than the binding energy of one of the said two electron orbits which is located at shorter distance from the atomic nucleus. The Figure of the present application diagrammatically shows the method of the present invention.

According to one embodiment of the present invention, a particular isotope can quantitatively be analyzed by measuring the dose of the gamma rays or internal conversion electrons from the substance after bombarding it with X rays or electrons, with any type of detectors for radioactivity such as GM counter.

Since each isotope has its characteristic energy levels, the excited states of the different isotopes have different values of excitation energy, spin, and parity. When a specimen is bombarded with X rays or electrons having such an energy sufficient as to satisfy the previously defined conditions for producing the excited state of the nuclei of the isotope to be quantitatively analysed, the nuclei of this isotope transits to the excited state while those of the other isotopes remain in their ground states. The nuclei in the excited state emit gamma rays or internal conversion electrons in their lifetime and go back to their ground state. This means that said isotope can only produce radioactivity by bombarding X rays or electrons. The number of the excited nuclei of the said isotope is proportional to its isotope abundance (concentration of said isotope) in the specimen and to the total radiation dose of the bombarding X rays or electrons. In order to establish a standard for the present method of measuring the concentration of a particular isotope, therefore, the radiation dose of the gamma rays or internal conversion electrons which are produced after bombarding the specimen of a chemically pure element with natural abundances of its isotopes is firstly measured by using a known dose of X rays or electrons. A standard which is a proportionality relation between the dose of the produced gamma rays or internal conversion electrons and the dose of the bombarding X rays or electrons can be determined from this experiment. In order to measure the concentration of said isotope in a test specimen, the radiation dose of gamma rays or internal conversion electrons which are produced after bombarding this specimen is measured by using a known dose of X rays or electrons. Since the proportionality relation between the irradiaing dose and the produced dose in the standard and the proportionality relation between the produced dose and the concentration of said isotope are known, the concentration of the particular isotope in the test specimen can be determined from the produced radiation dose. The dose of the produced gamma rays or internal conversion electrons increases with the energy of the bombarding X rays or electrons and the dose is represented by a saturation curve. It is therefore, preferable that the energy of the bombarding X rays or electrons is chosen so as to make the dose of the produced gamma rays or internal conversion electrons most efficiently, in addition to the previously defined conditions for the nuclear excitation. It will be understood by those skilled in the art that the bombarding conditions for X rays or electrons in the above measurements (such as duration of bombarding, constancy of the intensity of the bombarding X rays or electrons, shape of the gun, etc.) should be identical in the case of the standard specimen which contains the mixture of an element with the natural abundance of its isotopes, and in the case of the test specimen where the concentration of a particular isotope is analysed.

The term "X rays or electrons of the previously determined dose and energy" is used herein to mean "X rays or electrons which has an energy sufficient to satisfy the previously defined conditions for producing the excited state of the atomic nulceus but has a dose and energy chosen so as to be comparable with the above described propertionality relation in the standard."

According to another embodiment of this invention, a particular isotope can qualitatively be analyzed merely by detecting the emitted gamma rays or internal conversion electrons without measuring the dose thereof quantitatively. As a particular isotope is a specific nuclide having a specific atomic number and a specific mass, such nuclide can qualitatively be analyzed when this method is applied to a substance composed, in a chemical sense, of a mixture of different elements. In this case, this embodiment may be regarded as a method for the qualitative analysis of elements. In this embodiment, it is a matter of course that no necessity exists in measuring of the dose of the emitted gamma rays or internal conversion electrons but necessity exists in measurement of the energy thereof. Accordingly, the method for the qualitative analyses of nuclides and elements is obviously involved in the scope of this invention.

In this invention, detection of the gamma rays or internal conversion electrons and quantitative measurement of the dose thereof can be attained by using any type of detectors for radioactivity known in this art, for example, GM counter. Thus, the modes of measurement are not specifically limited in this invention.

Concerning the production of excited states of atomic nuclei, the method of this invention is based on the technical idea quite different from that in the prior art techniques and is not considered to be inferable easily from the knowledge in this art even by those skilled in the art. In the prior art methods, production of the excited state of atomic nuclei is exclusively carried out by conversion of nuclides (nuclear transmutation) in the nuclear reactions and nuclear decays, or by the Coulomb excitation with high-energy charged particles from the large-scale apparatus such as electron liniac. In contrast to this, the method of the present invention is directed to merely raising the energy of atomic nuclei from the ground state to the excited state by utilizing a physical means in a low-energy region such as an electron gun or X-ray tube.

An atom consists of an atomic nucleus and the bound electrons the number of which is equal to the atomic number Z. When the atomic is bombarded with X rays or electrons having energy higher than the binding energy of an orbital electron, this orbital electron is ejected out of the atom. Since the binding energy is different for every orbit, an electron of a particular orbit can selectively be kicked off by adjusting the energy of X rays or electrons to make an electron hole artificially for the relevant electron orbit. If the electron hole is made in a closed shell, the state of the atom becomes energetically unstable so that an electron of an outer orbit will immediately jump into the hole. In this electron transition, the energy corresponding to the difference between the binding energies of these two orbits is emitted in the form of X rays out of the atom. With a certain probability, this energy is transferred to an electron belonging to a far more outer orbit to let the electron overcome its binding energy and go out of the atom. This is called the Auger electron emission.

It has now been found, however, that when such electron hole is created in the closed shell (orbit) by bombardment of an atom with X rays or electrons, the excess energy in the subsequent electron transition is transferred to the nucleus, in competition with said well-known X-ray and Auger electron emissions, and the nucleus is excited by this energy absorption from its ground state to an excited state. This new surprising phenomenon found by the present inventors was called "Nuclear Excitation by Electron Transition", which is referred to herein simply as "nuclear excitation". By the way, this phenomenon may be called "Dynamic Excitation of Atomic Nucleus by Electron Transition" or "Inverse Internal Conversion Process."

By bombarding atoms with X rays or electrons, this phenomenon can take place only if the following specific conditions are fulfilled:

1. In order to produce the excited state of the nucleus,
   a. the relevant atoms have such a pair of the electron orbits that the difference between the nuclear excitation energy and the binding energy difference of these two orbits is small enough to introduce the nuclear excitation by electron transition, and
   b. the system of the nucleus, whose atomic number is represented by Z, and the (Z−1) electrons should satisfy the spin and parity conservation laws for the above pair of electron orbits and the nuclear ground and excited states.

2. The energy of the bombarding X rays or electrons should be larger than the binding energy of the electron which is more tightly bound with the nucleus among the above two orbits.

These conditions will be explained hereinafter by way of formulas wherein $I_g$ stands for the spin of the nucleus in the ground state, $\pi_g$ for the parity thereof, $\psi_g$ the wave function thereof, $I_e$ for the spin of the same nucleus in the excited state, $\pi_e$ for the parity thereof, $\psi_e$ for the wave function thereof, $E_N$ for the excitation energy thereof, $\phi_1$ for the wave function of an electron in the closed shell (orbit) which will be kicked off to form an electron hole by bombardment with X rays electrons, $J_1$ for the spin thereof, $\pi_1$ for the parity thereof, $E_1$ for the binding energy thereof, $\phi_2$ for the wave function of an electron in the outer shell which will jump into the electron hole in the orbit $**_1$, $J_2$ for the spin thereof, $\pi_2$ for the parity thereof, and $E_2$ for the binding energy thereof.

The condition required for energies can be expressed by $$E_N \approx E_1 - E_2.$$

The interaction energy $E_i$ of the system of the nucleus and an electron is expressed quantum mechanically by the non-diagonal element of a matrix $$E_i = (\phi_e \phi_1 | H_i | \phi_g \phi_2)$$

wherein $H_i$ is the Hamiltonian of the electromagnetic interactions of the system.

More particularly in the energy conditions, the probability of the nuclear excitation depends on $$(E_i/E_N - (E_1 - E_2)).$$

By expressing the above quantity as $x$, the case where a large absolute value of $x$ is preferable. In many cases, however, the absolute value of $x$ is smaller than unity. By denoting the value of $x$ for a particular isotope of a given element as $x_0$, the nuclear excitation can take place only for the isotope with $x_0$ if the other isotopes of the same element have $x$'s the values of which are less then about $0.1x_0$.

In many elements, $x$'s are actually less than $0.001x_0$ for the isotopes except for a particular isotope with $x_0$. (This means that the energy conditions, $EN \approx E_1 - E_2$, is not satisfied for these isotopes.) Accordingly, various practical applications of the method of this invention as will be given hereinafter can be performed without difficulty even though the value of $x_0$ itself is relatively small.

Next, the spin (or angular momentum) of the system of the nucleus and an electron should satisfy the conservation law for the spin vectors.

$$\vec{I_g} + \vec{J_1} = \vec{I_e} + \vec{J_2}$$

wherein the quantities expressed by the symbols with arrow are spin vectors for the physical states which have spin values expressed by corresponding regular faces, respectively. The parity of the system of the nucleus and electron should also satisfy the parity conservation law:

$$\pi_g \pi_1 = \pi_e \pi_2$$

In the nucleus of an atom of the atomic number Z which has an electron hole in a certain electron orbit and is thus surrounded by the (Z−1) orbital electrons, the conditions above described are given for the case where the (Z−1) orbital electrons can be represented by a single electron wave function corresponding to the orbit where the electron hole is made. More generally, the above conditions should be fulfilled by the resultant system of the nucleus and the (Z−1) electron system. In this case, $\phi_1$ and $\phi_2$ should be replaced by $\Phi_1$ and $\Phi_2$, respectively, where $\Phi_1$ and $\Phi_2$ stand for wave functions of the (Z−1) electron system before and after the electron transition. In the expression of $E_i$, $\phi_1$ should be replaced by $\Phi_2$ and $\phi_2$ by $\Phi_1$, due to the difference of the electron and its hole state.

It is necessary to produce the electron hole in an orbit for which the binding energy of the electron is $E_1$. It will easily be understood therefore that in the method of this invention the energy of the X rays or electrons for bombarding atoms should be larger than $E_1$. In the case of X rays, the energy is advantageously near $E_1$. In the case of electrons, however, the energy is advantageously 2–3 times as large as $E_1$. If this energy is less than $E_1$, the excited states of the nuclei of the relevant atoms will not be produced.

This invention will now be illustrated in more detail by way of an example. However, it is to be noted that the scope of this invention is not specifically limited to the extend illustrated and a wide variety of modifications are easily by those skilled in the art.

EXAMPLE 0.5 g. of pure natural osmium metal powder was compressed by the aid of a 26 ton press into a disk having a diameter of 23 mm. The disk was bombarded with electrons from an electron gun. The bombardment was carried out for 185 minutes at 28 μA with electrons of 74 kilo-electron volts, whereby the excited state of osmium 189 having a halflife of 5.7 hours was produced. Next, the bombardment of the disk with electrons from an electron gun was stopped, and the measurement of the 20 KeV internal conversion electrons was performed. The 20 kilo-electron volts internal conversion electrons emitted when the excited state were deexcited to the ground state was measured by an Aloka low background gas flow GM counter. As the result of measurement, the count number of 0.3 per minute was obtained. This experimental value accords with a theoretical calculation based on an estimated isotope abundance of 16% for osmium 189 in the test sample. This accords with the known values obtained by the prior art testing methods.

In a similar manner, uranium 235, neptunium 237, gold 197, iridium 193, tantalum 181, dysprosium 161 and tin 119 can be qualitatively or quantitatively analyzed.

What is claimed is:

1. A method for the analysis of isotopes which comprises bombarding a substance with X-rays or electrons of a previously determined dose and energy for analyzing an isotope in the substance, to produce an excited state of the atomic nuclei of the isotope and thereafter detecting the gamma rays or internal conversion electrons emitted from the substance when the atomic nuclei is deactivated from the excited state to the ground state, wherein the bombardment of the substance with X-rays or electrons is carried out under such conditions that (1) in the atoms selected to be produced in the excited state of their nuclei, (a) the difference between the nuclear excitation energy and the difference between the binding energies of adequatly selected two electron orbits is small enough to introduce the nuclear excitation by electron transition, and (b) the system of the nucleus and the electrons in the case of ionizing an orbital electron in said atoms should satisfy the spin and parity conservation laws, and (12) the energy of the bombarding X-rays or electrons should be larger than the binding of one of the said two electron orbits which is located at a shorter distance from the atomic nucleus.

2. The method according to claim 1 wherein the analysis of isotopes is conducted qualitatively by detecting the existance of the gamma rays or internal conversion electrons.

3. The method according to claim 1 wherein the analysis of isotopes is conducted quantitatively by measuring the dose of the gamma rays or internal conversion electrons.

4. A method according to claim 1 wherein the detection or measurement of the gamma rays or internal conversion electrons is perfomed by the aid of a GM counter.

* * * * *